(12) United States Patent
Uehara

(10) Patent No.: US 12,205,709 B2
(45) Date of Patent: Jan. 21, 2025

(54) MEDICAL IMAGE PROCESSING SYSTEM, MEDICAL IMAGE PROCESSING METHOD, IMAGE PROCESSING DISTRIBUTOR, AND PROGRAM

(71) Applicant: FUJIFILM Corporation, Tokyo (JP)

(72) Inventor: Daiki Uehara, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 367 days.

(21) Appl. No.: 17/903,043

(22) Filed: Sep. 6, 2022

(65) Prior Publication Data
US 2023/0114843 A1 Apr. 13, 2023

(30) Foreign Application Priority Data
Sep. 27, 2021 (JP) ................. 2021-156880

(51) Int. Cl.
  *G16H 30/20* (2018.01)
  *G16H 30/40* (2018.01)
  *G06T 7/00* (2017.01)

(52) U.S. Cl.
  CPC ............. *G16H 30/40* (2018.01); *G16H 30/20* (2018.01); *G06T 7/0012* (2013.01)

(58) Field of Classification Search
  CPC ....... G16H 30/40; G16H 30/20; G06T 7/0012
  See application file for complete search history.

(56) References Cited

U.S. PATENT DOCUMENTS

| | | | |
|---|---|---|---|
| 8,682,049 B2 | 3/2014 | Zhao et al. | |
| 9,430,828 B2 | 8/2016 | Wu et al. | |
| 10,078,727 B2 | 9/2018 | Wu et al. | |
| 2008/0065423 A1* | 3/2008 | Oda | G16H 30/20 705/3 |
| 2010/0266184 A1* | 10/2010 | Kitamura | G16H 30/40 382/131 |
| 2012/0239431 A1* | 9/2012 | Hayashi | G16H 10/60 705/3 |
| 2012/0287469 A1* | 11/2012 | Tomiyasu | H04N 1/00954 358/1.15 |
| 2013/0243282 A1* | 9/2013 | Sato | G16H 30/40 382/128 |
| 2014/0233815 A1* | 8/2014 | Sakaue | G16H 40/67 382/128 |
| 2019/0027244 A1 | 1/2019 | Wu et al. | |

FOREIGN PATENT DOCUMENTS

| | | |
|---|---|---|
| JP | 6047179 | 12/2016 |
| JP | 2018098538 | 6/2018 |

\* cited by examiner

*Primary Examiner* — Syed Haider
(74) *Attorney, Agent, or Firm* — JCIPRNET

(57) ABSTRACT

Each of a first server installed inside a medical institution and a second server installed on a network outside the medical institution includes a server program that receives a processing request for a medical image and that outputs a processing result by executing image processing corresponding to the processing request. An image processing distributor calculates a processing waiting time required until the processing result is obtained in a case where each server executes the image processing on the medical image, based on a required time required for executing the image processing on the medical image, a network connecting situation, and the number of processing requests in a processing waiting state inside each server, and transmits the processing request for the medical image to a server having a shorter processing waiting time.

19 Claims, 10 Drawing Sheets

MEDICAL IMAGE PROCESSING SYSTEM, MEDICAL IMAGE PROCESSING METHOD, IMAGE PROCESSING DISTRIBUTOR, AND PROGRAM

CROSS-REFERENCE TO RELATED APPLICATIONS

The present application claims priority under 35 U.S.C. § 119 to Japanese Patent Application No. 2021-156880 filed on Sep. 27, 2021. Each of the above application is hereby expressly incorporated by reference, in its entirety, into the present application.

BACKGROUND OF THE INVENTION

1. Field of the Invention

The present disclosure relates to a medical image processing system, a medical image processing method, an image processing distributor, and a non-transitory computer readable recording medium storing a program and particularly, to a computer system and an information processing technology suitable for processing of receiving a processing request for a medical image and outputting a processing result by executing image processing corresponding to the processing request.

2. Description of the Related Art

In the medical field, advances in image diagnostic apparatuses such as computed tomography (CT) apparatuses and magnetic resonance imaging (MRI) apparatuses have enabled image diagnosis using high-quality medical images having high resolution. Particularly, in recent years, use of artificial intelligence (AI) by utilizing a neural network trained by deep learning has improved accuracy of analysis processing for recognizing a lesion region or the like from an image or specifying a classification such as a disease name.

For example, the analysis processing such as computer aided diagnosis or computer aided detection (CAD) is generally prepared for each part such as a lung, a heart, a liver, and a brain or further for each detectable lesion, and executing the analysis processing requires a high-performance computer. JP6047179B suggests a system for providing an analysis processing service of a medical image by utilizing a cloud system.

JP2018-098538A discloses a system comprising a cloud server that provides a service, and an on-premises server. In a case where an instruction to execute a job is received from a utilizer, the system automatically switches the cloud server or the on-premises server used for job execution based on setting information of the job or on security information obtained at a time of executing the job.

SUMMARY OF THE INVENTION

For example, employing a type of service in which a central processing server for image analysis is installed on the cloud in order to provide various medical image processing functions such as lung CAD as a web service, and in which the central processing server performs image processing and outputs a result is considered. However, in a case of such a type of service, a time for transmitting and receiving images between a medical institution internal terminal and the central processing server is necessary in addition to a required time for the image processing.

Thus, additional time is required compared to the image processing performed by installing an image processing server inside a medical institution. In addition, in a case of processing requests from multiple utilizers to be processed via only the central processing server, a load is concentrated on the central processing server, and completion of each processing may take time. On the other hand, in a case of completing the image processing inside only the medical institution, all processing requests are concentrated on the image processing server inside the medical institution. In order to withstand the load, it is necessary to introduce a costly server, and the introduction may be difficult for small and medium-sized hospitals, clinics, and the like.

As a method of solving the above problem, a hybrid configuration of on-premises and the cloud is considered in which loads exerted on both of an image processing server (on-premises) side inside the medical institution and a central processing server (cloud) side are decreased by appropriately distributing processing between the image processing server inside the medical institution and the central processing server on the cloud.

In a case of employing such a hybrid configuration, for example, simply evenly distributing the processing requests may take more time than usual to obtain the processing result when the central processing server on the cloud is made to perform processing in a time slot in which a network line of each medical institution is congested. In order to avoid such an event, a solution of performing processing in a specific time slot using the image processing server inside the medical institution is considered.

However, in a fixed setting in which processing is performed using the image processing server inside the medical institution by determining a time slot in advance, in a case where the number of processing requests with respect to the image processing server inside the medical institution is increased in the time slot, processing resources of the image processing server inside the medical institution are strained, and a processing waiting time is increased unless the resources are increased by, for example, increasing the number of image processing servers inside the medical institution. Accordingly, in a case of distributing the processing using a simple method, a problem of an increase in processing waiting time of a whole system is expected.

In addition, the processing waiting time dynamically changes depending on a used facility, a time slot, and the like. Accordingly, it is desirable to minimize the processing waiting time of the whole system by appropriately distributing the processing to the image processing server inside the medical institution or to the central processing server on the cloud (outside the medical institution) in accordance with a situation.

The present disclosure is conceived in view of such a matter, and an object thereof is to provide a medical image processing system, a medical image processing method, an image processing distributor, and a non-transitory computer readable recording medium storing a program that can suppress a waiting time until completion of processing by distributing image processing to a server inside a medical institution or to a server outside the medical institution in accordance with a dynamically changing situation.

A medical image processing system according to an aspect of the present disclosure comprises a first server installed inside a medical institution, a second server installed on a network outside the medical institution, and an image processing distributor that distributes a processing request for a medical image to the first server or to the second server, in which each of the first server and the second server includes a server program that receives the processing request for the medical image and that outputs a processing result by executing image processing corresponding to the processing request, the image processing distributor includes one or more processors and one or more storage devices in which a program executed by the one or more processors is stored, and the one or more processors are configured to, by executing an instruction of the program, receive the processing request for the medical image, calculate a processing waiting time required until the processing result is obtained in a case where each server of the first server and the second server executes the image processing on the medical image, based on a required time required for executing the image processing on the medical image, a network connecting situation, and the number of processing requests in a processing waiting state inside each server, and transmit the processing request for the medical image to a server having a shorter processing waiting time out of the first server and the second server based on the calculated processing waiting time for each server.

In a case where the processing request for the medical image is received, the image processing distributor in the present aspect calculates a processing waiting time expected in a case where the first server performs processing, and a processing waiting time expected in a case where the second server performs processing. The calculation of the processing waiting time is performed based on the required time required for executing the image processing on the medical image, the network connecting situation, and the number of processing requests in the processing waiting state inside each server. The processing waiting time that reflects a dynamically changing situation is calculated. The processing request is transmitted to a server having a shorter waiting time until completion of the processing based on the calculated processing waiting time. Accordingly, the waiting time until the completion of the processing can be suppressed by appropriately distributing the processing to the first server inside the medical institution or to the second server outside the medical institution in accordance with a dynamically changing situation.

In the medical image processing system according to another aspect of the present disclosure, the second server may be configured to be shared and used by a plurality of the medical institutions.

In the medical image processing system according to another aspect of the present disclosure, the image processing distributor may be configured to receive the processing request for the medical image from a terminal connected to a first network inside the medical institution. The first network may be a local area network constructed inside the medical institution. In addition, a plurality of terminals may be connected to the first network, and the processing request may be output from each terminal.

In the medical image processing system according to another aspect of the present disclosure, an image management server that stores the medical image may be configured to be installed inside the medical institution. The image processing can be performed by transmitting the medical image stored in the image management server to the first server or to the second server.

In the medical image processing system according to another aspect of the present disclosure, the processing result of the image processing executed by the first server or by the second server may be configured to be stored in the image management server.

In the medical image processing system according to another aspect of the present disclosure, the second server may be configured to acquire the medical image from the image processing distributor through a second network as the network outside the medical institution.

In the medical image processing system according to another aspect of the present disclosure, at least one of the first server, the second server, or the image processing distributor may be configured to hold a cache file of the medical image received in the past.

In the medical image processing system according to another aspect of the present disclosure, the one or more processors may be configured to calculate the processing waiting time based on whether or not transmission and reception of the medical image that is a processing target are necessary. For example, in a case where the processing target medical image is held as a cache file, the transmission and reception of the medical image may not be necessary. In a case of transmitting and receiving the processing target medical image, it is preferable that the processing waiting time is configured to be calculated including a time required for the transmission and reception.

In the medical image processing system according to another aspect of the present disclosure, the one or more processors may be configured to calculate a first processing waiting time required until the processing result is obtained in a case of executing the image processing via the first server, and a second processing waiting time required until the processing result is obtained in a case of executing the image processing via the second server, and decide a transmission destination of the processing request based on a comparison between the calculated first processing waiting time and the calculated second processing waiting time.

A medical image processing method according to another aspect of the present disclosure is a medical image processing method executed by a computer system including a first server installed inside a medical institution, and a second server installed on a network outside the medical institution, each of the first server and the second server including a server program that receives a processing request for a medical image and that outputs a processing result by executing image processing corresponding to the processing request, the medical image processing method comprising, via one or more processors included in the computer system, receiving the processing request for the medical image, calculating a processing waiting time required until the processing result is obtained in a case where each server of the first server and the second server executes the image processing on the medical image, based on a required time required for executing the image processing on the medical image, a network connecting situation, and the number of processing requests in a processing waiting state inside each server, and transmitting the processing request for the medical image to a server having a shorter processing waiting time out of the first server and the second server based on the calculated processing waiting time for each server.

An image processing distributor according to another aspect of the present disclosure is an image processing distributor that distributes a processing request for a medical image to a first server installed inside a medical institution or to a second server installed on a network outside the medical institution, each of the first server and the second server including a server program that receives the processing request for the medical image and that outputs a processing result by executing image processing corresponding to the processing request, the image processing distributor comprising one or more processors and one or more storage devices in which a program executed by the one or more processors is stored, in which the one or more processors are configured to, by executing an instruction of the program, receive the processing request for the medical image, calculate a processing waiting time required until the processing result is obtained in a case where each server of the first server and the second server executes the image processing on the medical image, based on a required time required for executing the image processing on the medical image, a network connecting situation, and the number of processing requests in a processing waiting state inside each server, and transmit the processing request for the medical image to a server having a shorter processing waiting time out of the first server and the second server based on the calculated processing waiting time for each server.

A non-transitory computer readable recording medium storing a program according to another aspect of the present disclosure is a program causing a computer to implement a function of receiving a processing request for a medical image, and a function of distributing the received processing request to a first server installed inside a medical institution or to a second server installed on a network outside the medical institution, each of the first server and the second server including a server program that outputs a processing result by executing image processing corresponding to the processing request, the program causing the computer to implement a function of calculating a processing waiting time required until the processing result is obtained in a case where each server of the first server and the second server executes the image processing on the medical image, based on a required time required for executing the image processing on the medical image, a network connecting situation, and the number of processing requests in a processing waiting state inside each server, and a function of transmitting the processing request for the medical image to a server having a shorter processing waiting time out of the first server and the second server based on the calculated processing waiting time for each server.

According to the present disclosure, the processing waiting time can be suppressed by distributing the image processing to the first server inside the medical institution or to the second server outside the medical institution in accordance with a dynamically changing situation.

DESCRIPTION OF THE PREFERRED EMBODIMENTS

Hereinafter, a preferred embodiment of the present invention will be described in accordance with the appended drawings.

Summary of Medical Image Processing System

Figure 1:
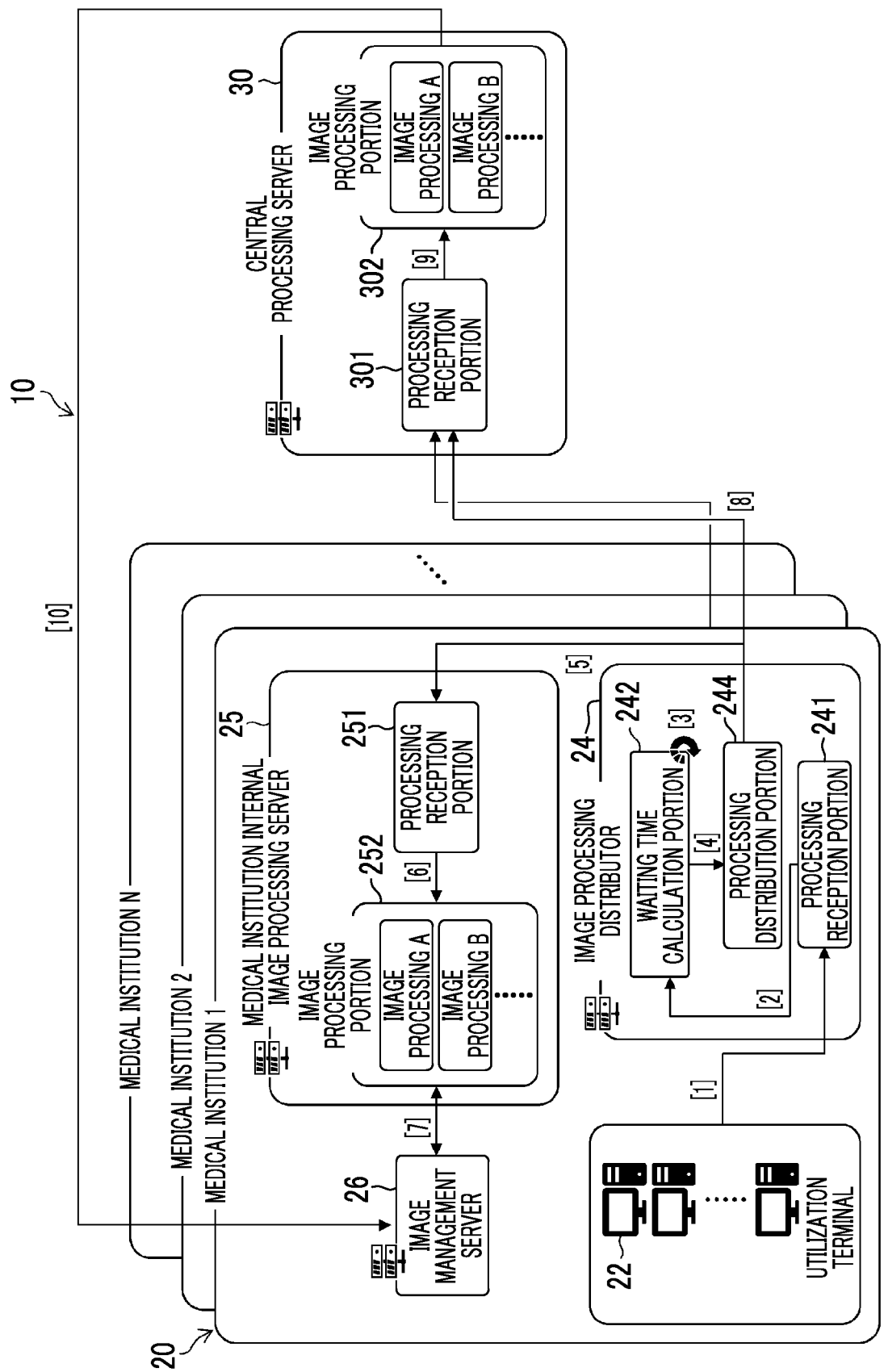
FIG. 1 is a block diagram illustrating a summary of a configuration and an operation of a medical image processing system according to an embodiment.

FIG. 1 is a block diagram illustrating a summary of a configuration and an operation of a medical image processing system 10 according to the embodiment. The medical image processing system 10 includes a medical information system 20 constructed inside each medical institution of a plurality of medical institutions and a central processing server 30 installed on a network outside the medical institutions. The description of "medical institution 1", "medical institution 2", . . . , "medical institution N" illustrated in FIG. 1 represents that N medical institutions are present. For example, the medical institution is a hospital, a clinic, a medical research center, or a medical check-up center.

The medical information system 20 of each medical institution includes one or more utilization terminals 22, an image processing distributor 24, a medical institution internal image processing server 25, and an image management server 26. The utilization terminal 22 is a terminal with which a medical image processing service provided using the medical institution internal image processing server 25 and the central processing server 30 can be utilized. Client software for utilizing functions of a medical image processing server group including the medical institution internal image processing server 25 and the central processing server 30 is constructed in the utilization terminal 22.

Here, the utilization terminal 22 refers to a calculation resource present in a network in which data inside the medical institution can be safely accessed. The terminal may not be physically present inside the medical institution. The utilization terminal 22 may be a workstation, a personal computer, a tablet terminal, or the like. In addition, the "client software" may be software with which a medical image processing server cluster can be utilized, regardless of a form thereof. The client software may be a dedicated application or a general-purpose web browser or the like. For example, the utilization terminal 22 may be an interpretation terminal such as a medical image viewer. It is preferable that the medical information system 20 is configured to include a plurality of utilization terminals 22. The utilization terminal 22 is an example of a "terminal" according to the embodiment of the present disclosure.

The image processing distributor 24 includes a processing reception portion 241, a waiting time calculation portion 242, and a processing distribution portion 244. The image processing distributor 24 receives a request to perform image processing on a medical image from the utilization terminal 22, calculates a processing waiting time of each of the medical institution internal image processing server 25 and the central processing server 30, and decides a transmission destination of a processing request by determining which server performs processing earlier (has a shorter processing waiting time). In addition, the image processing distributor 24 acquires a processing target image from the image management server 26 as needed and transmits the processing target image to the medical institution internal image processing server 25 or to the central processing server 30. A function (image processing distribution function) of the image processing distributor 24 will be described in detail later.

The image processing distributor 24 may be an environment in which software providing the image processing distribution function operates, regardless of a form of a server in which the software is loaded. The software is synonymous with a program.

An image processing program for processing the medical image is constructed on each server of the medical institution internal image processing server 25 of each medical institution and the central processing server 30. Each server may be an environment in which the image processing program operates, and may be a physical machine or a virtual machine. The image processing program loaded into the medical institution internal image processing server 25 and the image processing program loaded into the central processing server 30 may be server programs providing the same medical image processing service.

The medical institution internal image processing server 25 is a server that may be exclusively used by the medical institution for each medical institution, and is installed inside a facility of the medical institution. The medical institution internal image processing server 25 includes a processing reception portion 251 and an image processing portion 252, receives the processing request transmitted from the image processing distributor 24, and performs the image processing on a target medical image in accordance with the received processing request. The processing reception portion 251 includes a waiting matrix (queue) in which the received processing request is queued.

The image processing portion 252 may include a processing module that performs a plurality of types of image processing. The description of "image processing A" and "image processing B" in FIG. 1 represents processing modules that perform different types of image processing. The medical institution internal image processing server 25 is an example of a "first server" according to the embodiment of the present disclosure.

The central processing server 30 is a server that is shared and used by the plurality of medical institutions. The central processing server 30 is installed on the network (for example, on the cloud) outside the medical institutions. The central processing server 30 includes a processing reception portion 301 and an image processing portion 302 like the medical institution internal image processing server 25. The central processing server 30 receives the processing request transmitted from the image processing distributor 24 of each medical institution, performs the image processing on the target medical image in accordance with the received processing request, and outputs a processing result. The central processing server 30 is an example of a "second server" according to the embodiment of the present disclosure.

That is, the medical image processing system 10 provides the medical image processing service via a hybrid configuration in which the on-premises medical institution internal image processing server 25 and the central processing server 30 on the cloud are combined. Here, the on-premises means an apparatus installed inside each medical institution. On the other hand, the cloud means arrangement on a network for utilization from the plurality of medical institutions.

The image management server 26 is a server for storing the medical image. The processing result of the image processing by the medical institution internal image processing server 25 or by the central processing server 30 may be transmitted to the image management server 26 inside the medical institution of a processing request source and may be stored in the image management server 26 by linking the processing result to the processing target image.

Description of Medical Image Processing Method

The operation of the medical image processing system 10 will be schematically described using a flow of Procedure [1] to Procedure [10] illustrated in FIG. 1 as an example.

Procedure [1]: First, the processing request for the medical image is transmitted from the utilization terminal 22 inside the medical institution toward the processing reception portion 241 of the image processing distributor 24. The processing request includes information for specifying the processing target image and information for providing an instruction for the content of processing.

Procedure [2]: The processing reception portion 241 of the image processing distributor 24 receives the processing request from the utilization terminal 22 and transmits received information to the waiting time calculation portion 242.

Procedure [3]: The waiting time calculation portion 242 calculates a waiting time for the processing. At this point, the waiting time calculation portion 242 may calculate the waiting time after the processing request for the medical image is actually received, that is, after a need to calculate the waiting time occurs, or, for example, may periodically calculate the waiting time in advance even in a case where the actual processing request is not received.

Figure 2:
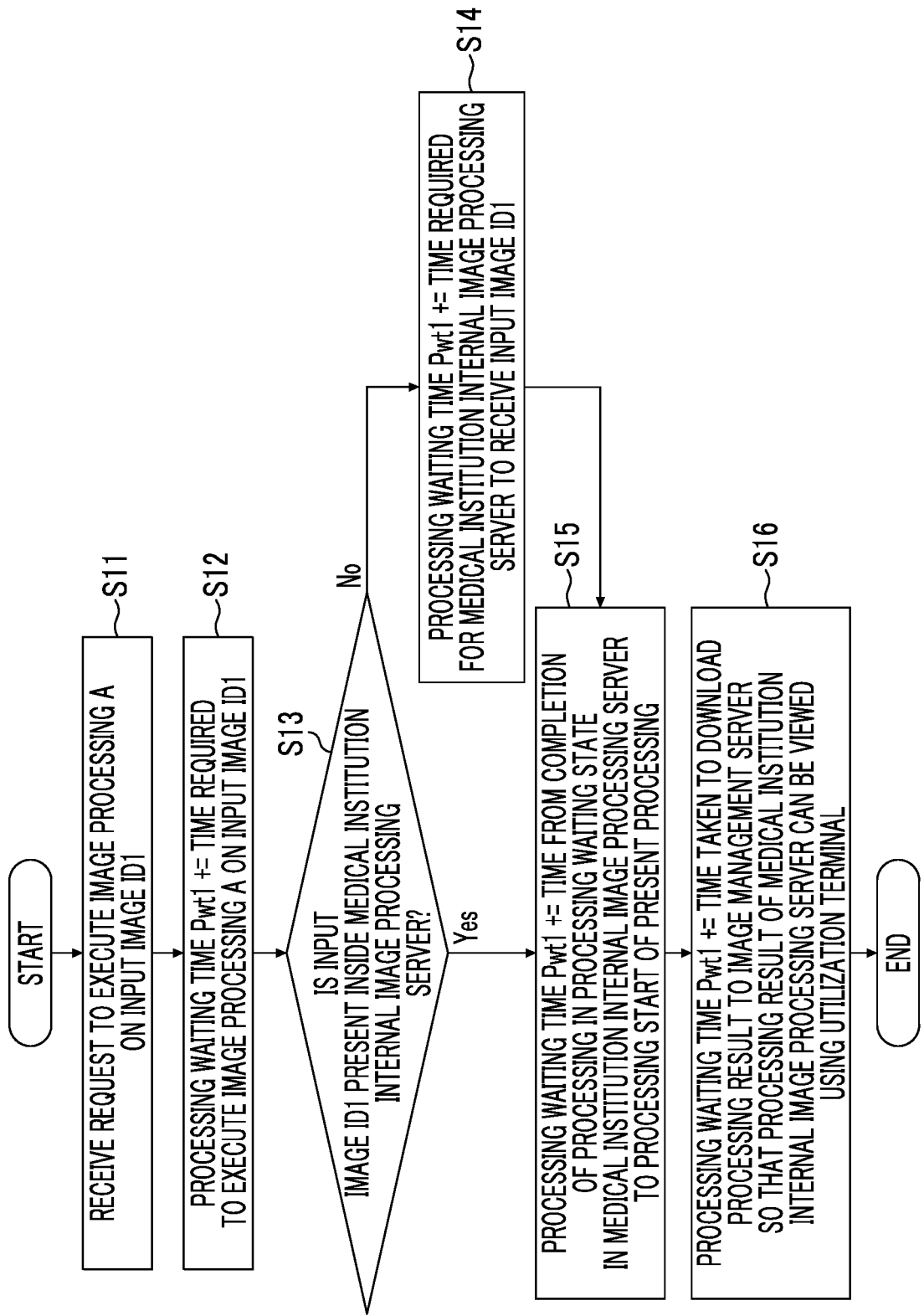
FIG. 2 is a flowchart illustrating a calculation example of a waiting time in a case of performing image processing via a medical institution internal image processing server.
Figure 3:
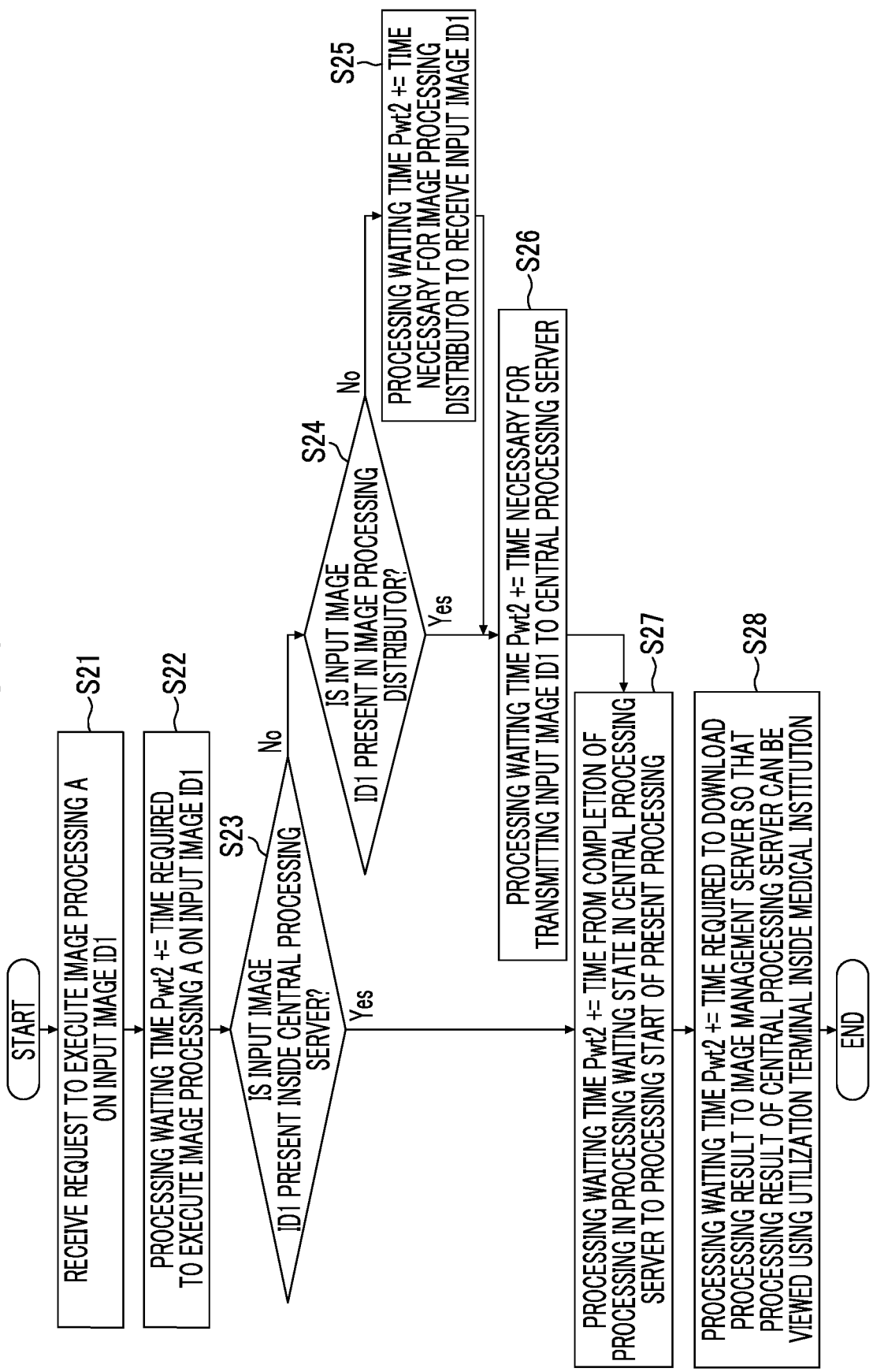
FIG. 3 is a flowchart illustrating a calculation example of the waiting time in a case of performing the image processing via a central processing server.

The waiting time calculation portion 242 calculates each of the waiting time in a case of performing the processing using the medical institution internal image processing server 25 and the waiting time in a case of performing the processing using the central processing server 30. At this point, it is desirable that a required time required for executing the image processing on each medical image is not a fixed value and, for example, can be set such that the required time is increased in proportion to a file size of the processing target image. In addition, since a time required to transmit and receive the processing target image dynamically changes in accordance with a network connecting situation of each medical institution, a program for measuring the required time by actually transmitting and receiving the image is operated in the background to periodically obtain a time required for the image processing. A specific example of a calculation flow in the waiting time calculation portion 242 will be described later (FIG. 2 and FIG. 3).

In addition, the waiting time obtained by the waiting time calculation portion 242 may be displayed on the utilization terminal 22 or the like so that a utilizer perceives how long the waiting time is.

Procedure [4]: A calculation result of the waiting time calculation portion 242 is transmitted to the processing distribution portion 244. The processing distribution portion 244 decides the transmission destination of the processing request by determining whether to perform the processing in the medical institution internal image processing server 25 or perform the processing in the central processing server 30 based on the calculation result of the waiting time calculation portion 242.

Procedure [5]: As a result of calculating the waiting time, in a case where performing the processing in the medical institution internal image processing server 25 completes the processing earlier, the processing distribution portion 244 transmits the processing request to the medical institution internal image processing server 25.

Procedure [6]: In a case where the processing request is received from the processing distribution portion 244, the processing reception portion 251 of the medical institution internal image processing server 25 causes the image processing portion 252 to execute the image processing. The image processing portion 252 starts the image processing in accordance with an instruction from the processing reception portion 251. In a case where an input image (processing target image) necessary for the processing needs to be acquired, the medical institution internal image processing server 25 acquires the processing target image from the image management server 26. In a case where the processing target image is stored in a cache of the medical institution internal image processing server 25, the acquisition of the image from the image management server 26 is not necessary.

Procedure [7]: The image processing portion 252 executes the image processing corresponding to the processing request and stores the processing result in the image management server 26. The processing result may be an image (processing result image) obtained by the image processing, information other than an image, or a combination thereof. Examples of the information other than the image include classification information, labeling information, positional information of a region of interest, or a candidate of a medical opinion corresponding to the medical image.

Here, in a case where a plurality of types of processing A-1, A-2, . . . , A-n need to be internally executed in order to output a result of a certain processing request A received in Procedure [1], the calculation of the waiting time and the determination of to which of the medical institution internal image processing server 25 or the central processing server 30 the processing request is transmitted may be performed for each of the plurality of types of processing A-1, A-2, . . . , A-n. For example, the waiting time of each of the n types of processing A-1, A-2, . . . , A-n may be calculated, and a determination may be made such that in a case where a result indicating that transmission to the central processing server 30 finishes the processing earlier is obtained for at least a majority of n, the processing request A is transmitted to the central processing server 30, and conversely, in a case where a result indicating that transmission to the medical institution internal image processing server 25 finishes the processing earlier is obtained for at least a majority, the processing request A is transmitted to the medical institution internal image processing server 25.

On the other hand, as a result of calculating the waiting time in the waiting time calculation portion 242, in a case where performing the processing in the central processing server 30 completes the processing earlier based on the determination in Procedure [4], Procedures [8] to [10] are applied instead of Procedures [5] to [7].

Procedure [8]: As a result of calculating the waiting time, in a case where performing the processing in the central processing server 30 completes the processing earlier, the processing distribution portion 244 transmits the processing request to the central processing server 30. At this point, in a case where the processing target image needs to be transmitted to the central processing server 30, the processing distribution portion 244 acquires the processing target image from the image management server 26 as needed and transmits the processing request to the central processing server 30 together with the processing target image. In a case where the processing target image is stored in a cache of the central processing server 30, the transmission of the image from the processing distribution portion 244 is not necessary.

Procedure [9]: In a case where the processing request is received from the processing distribution portion 244, the processing reception portion 301 of the central processing server 30 causes the image processing portion 302 to execute the image processing in accordance with the received processing request. The image processing portion 302 starts the image processing based on an instruction from the processing reception portion 301.

Procedure [10]: The image processing portion 302 executes the image processing corresponding to the processing request and stores the processing result in the image management server 26. The processing result is transmitted to the image management server 26 as soon as the processing on the central processing server 30 is completed.

The processing result of the central processing server 30 or of the medical institution internal image processing server 25 can be displayed on the utilization terminal 22 of the processing request source and can further be displayed on other utilization terminals 22 inside the same medical institution.

Example of Calculation Flow of Waiting Time: In Case of Performing Processing Inside Medical Institution Internal Image Processing Server 25

FIG. 2 is a flowchart illustrating an example of waiting time calculation processing executed in the waiting time calculation portion 242 of the image processing distributor 24. The flowchart in FIG. 2 illustrates a calculation flow of the waiting time in a case of performing the processing inside the medical institution internal image processing server 25. Here, a case will be illustratively described where the input image as the processing target image is an image (hereinafter, referred to as an input image ID1) specified by ID number=1, and the requested type of image processing is processing referred to as image processing A.

In step S11, the waiting time calculation portion 242 receives a request to execute the image processing A on a certain input image ID1.

The waiting time calculation portion 242 that receives the request to execute the image processing A on the input image ID1 adds a time (hereinafter, referred to as a "first image processing execution required time") required to execute the image processing A on a certain input image ID1 to a processing waiting time Pwt1 as a processing time in step S12. A symbol "+=" in an expression represents addition of a right-side value to a current value of a left-side value.

For the first image processing execution required time, in a case of image processing in which processing takes more time as an input image size is increased as described in Procedure [3], a configuration in which the processing time is dynamically calculated in accordance with the image size is desired. The first image processing execution required time is an example of a "required time" according to the embodiment of the present disclosure. The first image processing execution required time may be construed as an expected processing time estimated as a time required to execute the image processing.

Next, in step S13, the waiting time calculation portion 242 determines whether or not the input image ID1 is present inside the medical institution internal image processing server 25. In a case of performing the processing by the medical institution internal image processing server 25, an input image ID of the processing target needs to be present inside the medical institution internal image processing server 25. In a case where the input image ID1 is not present inside the medical institution internal image processing server 25, the input image ID1 needs to be transmitted to the medical institution internal image processing server 25 from the image management server 26.

In a case where this transmission is necessary, that is, in a case where a determination result of step S13 is a No determination, the waiting time calculation portion 242 transitions to step S14.

In step S14, the waiting time calculation portion 242 adds a time (hereinafter, referred to as a "first input image reception required time") required for the medical institution internal image processing server 25 to receive the input image ID from the image management server 26, to the processing waiting time Pwt1 as the waiting time. The first input image reception required time is a time required for transmitting the input image ID. At this point, the time required for transmission dynamically changes in accordance with a congestion situation of the network at the moment of transmission, and the congestion situation also varies depending on a utilizing facility.

Accordingly, it is desirable that the waiting time calculation portion 242 can calculate how long it takes to perform the transmission and how large a size of data is as a value of waiting time calculation at a time of the subsequent transmission or later, by measuring the actual time required to complete the transmission. After step S14, the waiting time calculation portion 242 transitions to step S15.

On the other hand, in a case where the determination result of step S13 is a Yes determination as in a case where the input image ID is stored in the cache of the medical institution internal image processing server 25, the waiting time calculation portion 242 transitions to step S15.

In step S15, since all processing already in a processing waiting state inside the medical institution internal image processing server 25 needs to be processed before the currently received processing request is processed, the waiting time calculation portion 242 adds a time (hereinafter, referred to as a "first existing processing completion waiting time") from processing of all processing in the processing waiting state inside the medical institution internal image processing server 25 to a processing start of the present processing, to the processing waiting time Pwt1. At this point, a time until all existing processing requests in the processing waiting state are processed may be obtained by adding up a waiting time of each processing request currently in the processing waiting state at each moment of processing, or a total waiting time value of a processing waiting queue may be updated each time a new processing request arrives in the processing waiting queue. The first existing processing completion waiting time is calculated by reflecting the number of processing requests in the processing waiting state inside the medical institution internal image processing server 25. After step S15, the waiting time calculation portion 242 transitions to step S16.

The result image may need to be downloaded to the image management server 26 so that the processing result of the medical institution internal image processing server 25 can be viewed using the utilization terminal 22 inside the medical institution. In step S16, the waiting time calculation portion 242 also adds a time (hereinafter, referred to as a "first result reception required time") required for the download to the processing waiting time Pwt1. For the first result reception required time, the waiting time can be dynamically calculated by periodically measuring a time required for the download, as in a case of transmitting the processing target image to the medical institution internal image processing server 25. The first result reception required time is calculated by reflecting the network connecting situation inside the medical institution. After step S16, the waiting time calculation portion 242 finishes the flowchart in FIG. 2.

According to the calculation flow illustrated in FIG. 2, the processing waiting time Pwt1 finally calculated by passing through a processing path of a case where the determination result of step S13 is a Yes determination is first image processing execution required time+first existing processing completion waiting time+first result reception required time. On the other hand, the processing waiting time Pwt1 finally calculated by passing through a processing path of a case where the determination result of step S13 is a No determination is first image processing execution required time+first input image reception required time+first existing processing completion waiting time+first result reception required time.

A configuration in which whether or not to add the "first input image reception required time" is controlled in accordance with the determination result of step S13 is an example of an aspect "calculate a processing waiting time based on whether or not transmission and reception of a medical image are necessary" according to the embodiment of the present disclosure. The processing waiting time Pwt1 calculated in accordance with the calculation flow illustrated in FIG. 2 is an example of a "first processing waiting time" according to the embodiment of the present disclosure.

Example of Calculation Flow of Waiting Time: In Case of Performing Processing Inside Central Processing Server 30

FIG. 3 is a flowchart illustrating an example of the waiting time calculation processing executed in the waiting time calculation portion 242 of the image processing distributor 24. The flowchart in FIG. 3 illustrates a calculation flow of the waiting time in a case of performing the processing inside the central processing server 30. Here, a case where the input image as the processing target image is the input image ID1, and where the requested type of image processing is processing referred to as the image processing A will be illustratively described as in FIG. 2.

In step S21, the waiting time calculation portion 242 receives a request to execute the image processing A on a certain input image ID1. The waiting time calculation portion 242 that receives the request to execute the image processing A on the input image ID1 obtains a time (hereinafter, referred to as a "second image processing execution required time") required to execute the image processing A on the input image ID1 and adds the obtained time to a processing waiting time Pwt2 as the waiting time in step S22.

As in step S12 in FIG. 2, a configuration in which the second image processing execution required time is dynamically calculated in accordance with the image size is desired. The second image processing execution required time is an example of the "required time" according to the embodiment of the present disclosure. The second image processing execution required time may be construed as the expected processing time estimated as a time required to execute the image processing.

Next, in step S23, the waiting time calculation portion 242 determines whether or not the input image ID1 is present inside the central processing server 30. In a case where a determination result of step S23 is a No determination, the waiting time calculation portion 242 transitions to step S24.

In step S24, the waiting time calculation portion 242 determines whether or not the input image ID1 is present inside the image processing distributor 24. In a case where a determination result of step S24 is a No determination, the waiting time calculation portion 242 transitions to step S25.

In step S25, the waiting time calculation portion 242 adds a time (hereinafter, referred to as a "second input image reception required time") required for the image processing distributor 24 to receive the input image ID from the image management server 26, to the processing waiting time Pwt2. After step S25, the waiting time calculation portion 242 transitions to step S26.

The reason why step S24 and step S25 are necessary is as follows. That is, in the present embodiment, in transmitting the processing target image to the central processing server 30, the image is transmitted to the central processing server 30 from the image processing distributor 24. However, in order to transmit the image, first, the image of a transmission target has to be present inside the image processing distributor 24 of a transmission source. Otherwise, the transmission cannot be performed. Accordingly, the determination in step S24 is performed, and in a case where the processing target image is not present in the image processing distributor 24, the processing target image needs to be transmitted to the image processing distributor 24 from the image management server 26. Thus, this waiting time for transmission (second input image reception required time) is added to the processing waiting time Pwt2.

On the other hand, in a case where the determination result of step S24 is a Yes determination as in a case where the input image ID is stored in a cache of the image processing distributor 24, the processing target image does not need to be transmitted to the image processing distributor 24 from the image management server 26. Thus, the waiting time calculation portion 242 transitions to step S26.

In step S26, the waiting time calculation portion 242 adds a time (hereinafter, referred to as an "input image transmission required time") required for transmitting the input image ID1 to the central processing server 30 from the image processing distributor 24, to the processing waiting time Pwt2. This time required for transmission dynamically changes depending on the congestion situation of the network of each facility. Thus, even in obtaining the input image transmission required time, as in the example described in step S14 in FIG. 2, it is desirable that the time required for the transmission is dynamically obtained by periodically measuring a network speed using dummy data or the like.

After step S26, the waiting time calculation portion 242 transitions to step S27. In addition, in a case where the determination result of step S23 is a Yes determination as in a case where the input image ID is stored in the cache of the central processing server 30, the waiting time calculation portion 242 transitions to step S27.

In step S27, the waiting time calculation portion 242 adds a waiting time (hereinafter, referred to as a "second existing processing completion waiting time") from completion of all processing already in the processing waiting state inside the central processing server 30 until processing of the current processing request to be transmitted can be started, to the processing waiting time Pwt2. The second existing processing completion waiting time is calculated by reflecting the number of processing requests in the processing waiting state inside the central processing server 30.

Next, in step S28, as in step S16 in FIG. 2, the waiting time calculation portion 242 adds a time (hereinafter, referred to as a "second result reception required time") required for downloading the processing result to the image management server 26 so that the processing result can be viewed using the utilization terminal 22 inside the medical institution in a case of performing the image processing via the central processing server 30. For this time required for the download, it is desirable that the waiting time can be dynamically calculated by periodically measuring a time required for the download as in a case of transmitting the processing target image to the central processing server 30. After step S28, the waiting time calculation portion 242 finishes the flowchart in FIG. 3.

According to the calculation flow illustrated in FIG. 3, the processing path is divided into three patterns depending on the determination result of each of step S23 and step S24, and the finally calculated processing waiting time Pwt2 varies in accordance with the three patterns of the processing path. That is, the processing waiting time Pwt2 finally calculated by passing through a processing path of a case where the determination result of step S23 is a Yes determination is second image processing execution required time+second existing processing completion waiting time+second result reception required time.

The processing waiting time Pwt2 finally calculated by passing through a processing path of a case where the determination result of step S23 is a No determination and where the determination result of step S24 is a Yes determination is second image processing execution required time+input image transmission required time+second existing processing completion waiting time+second result reception required time. The processing waiting time Pwt2 finally calculated by passing through a processing path of a case where the determination result of step S23 is a No determination and where the determination result of step S24 is a No determination is second image processing execution required time+second input image reception required time+input image transmission required time+second existing processing completion waiting time+second result reception required time.

The configuration in which whether or not to add the "first input image reception required time" is controlled in accordance with the determination result of step S13 is an example of the aspect "calculate the processing waiting time based on whether or not the transmission and reception of the medical image are necessary" according to the embodiment of the present disclosure. A configuration in which whether or not to add the "second input image reception required time" is controlled in accordance with the determination result of step S23, and a configuration in which whether or not to add the "input image transmission required time" is controlled in accordance with the determination result of step S24 are an example of the aspect "calculate the processing waiting time based on whether or not the transmission and reception of the medical image are necessary" according to the embodiment of the present disclosure. The processing waiting time Pwt2 calculated in accordance with the calculation flow illustrated in FIG. 3 is an example of a "second processing waiting time" according to the embodiment of the present disclosure.

Calculation results of the flowcharts in FIG. 2 and FIG. 3 are transmitted to the processing distribution portion 244, and a server that executes the image processing is determined.

Example of Processing Flow in Processing Distribution Portion 244

Figure 4:
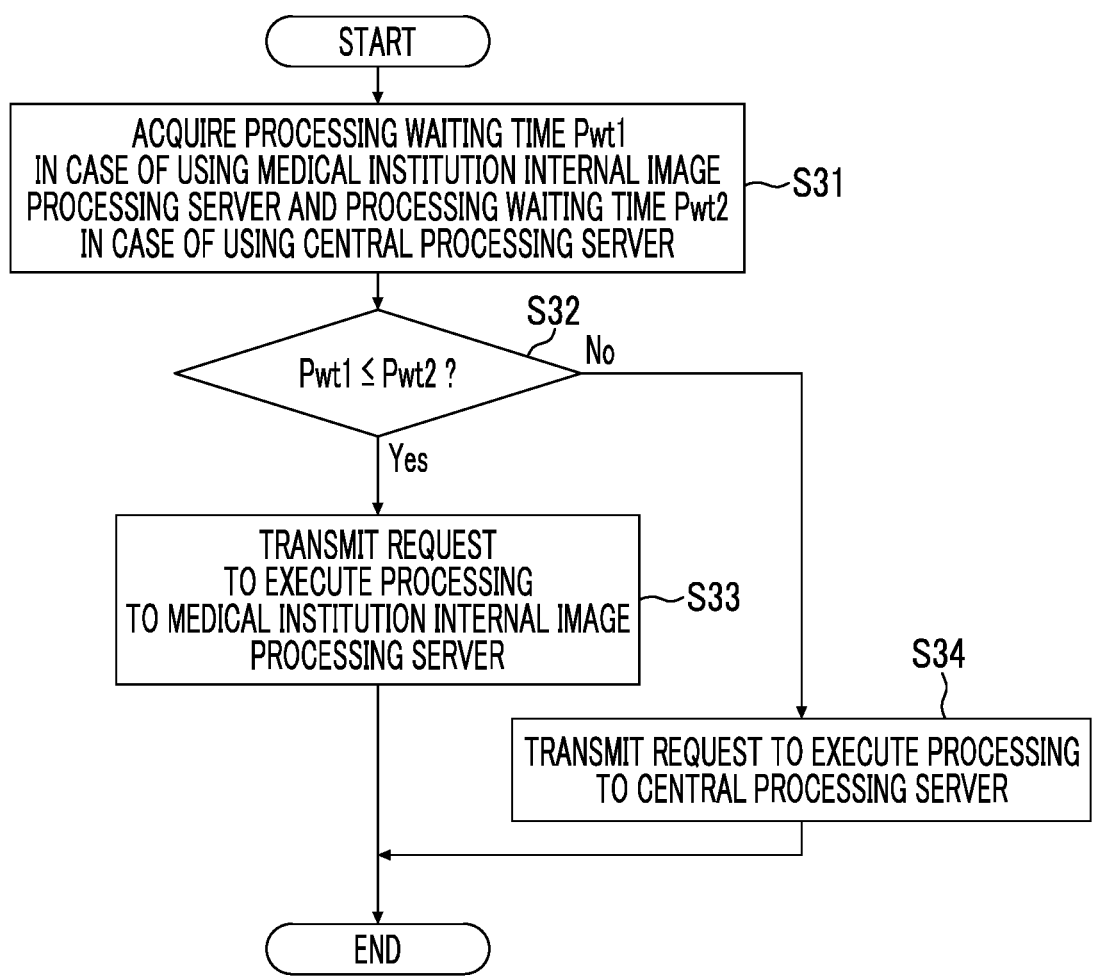
FIG. 4 is a flowchart illustrating an example of processing executed by a processing distribution portion of an image processing distributor.

FIG. 4 is a flowchart illustrating an example of processing executed by the processing distribution portion 244 of the image processing distributor 24. In step S31, the processing distribution portion 244 acquires the processing waiting time Pwt1 in a case of using the medical institution internal image processing server 25 and the processing waiting time Pwt2 in a case of using the central processing server 30 from the waiting time calculation portion 242.

In step S32, the processing distribution portion 244 compares magnitudes of Pwt1 and Pwt2. In a case where Pwt1≤Pwt2 is satisfied, the processing distribution portion 244 transitions to step S33. In step S33, the processing distribution portion 244 transmits a request to execute the processing to the medical institution internal image processing server 25.

On the other hand, in a case where the determination in step S32 results in Pwt1>Pwt2, the processing distribution portion 244 transitions to step S34, and the processing distribution portion 244 transmits the request to execute the processing to the central processing server 30.

After step S33 or step S34, the processing distribution portion 244 finishes the flowchart in FIG. 4.

The request (processing request) to execute the processing is transmitted from the processing distribution portion 244 to a server having a shorter processing waiting time out of the medical institution internal image processing server 25 and the central processing server 30 based on the calculation results of the processing waiting time Pwt1 and the processing waiting time Pwt2. Accordingly, the processing waiting time as a whole system is minimized.

System Configuration Example

Figure 5:
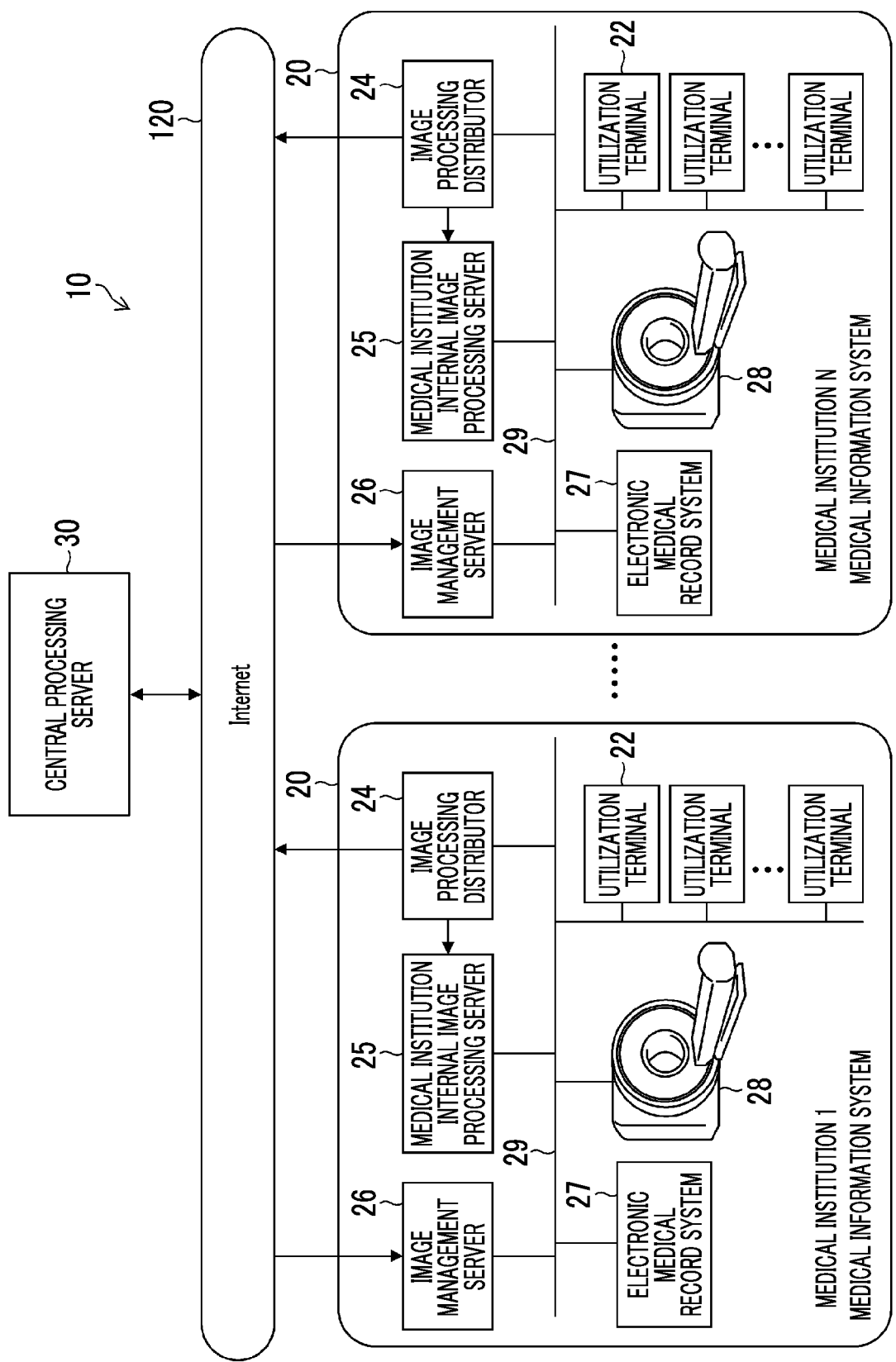
FIG. 5 is a diagram schematically illustrating a system configuration example of the medical image processing system according to the embodiment.

FIG. 5 is a diagram schematically illustrating a system configuration example of the medical image processing system 10. In FIG. 5, while an example in which the medical information system 20 having the same configuration is constructed in each of the plurality of medical institutions is illustrated for simplification of illustration, a medical information system having different configurations for each medical institution may be constructed.

The medical information system 20 illustrated in FIG. 5 may include an electronic medical record system 27 and one or more modalities 28 in addition to the plurality of utilization terminals 22, the image processing distributor 24, the medical institution internal image processing server 25, and the image management server 26 described using FIG. 1. These elements are connected to a local area network 29 inside the medical institution. The local area network 29 is an example of a "first network" according to the embodiment of the present disclosure.

The modality 28 is an apparatus that captures an examination image. The modality 28 includes an apparatus that images an examination target part of a subject to generate an examination image representing the part and that outputs the image by adding accessory information defined by digital imaging and communication in medicine (DICOM) standard to the image. Specific examples of the modality 28 include a computed tomography (CT) apparatus, a magnetic resonance imaging (MRI) apparatus, an angiography X-ray diagnostic apparatus, a positron emission tomography (PET) apparatus, an ultrasonic apparatus, a computed radiography (CR) apparatus using a flat X-ray detector (flat panel detector: FPD), a mammography apparatus, and an endoscope apparatus.

The medical information system 20 may include a plurality of types of modalities 28. Various combinations of the types and the number of modalities 28 are available for each medical institution.

For example, the image management server 26 may be a server that operates in accordance with DICOM specifications. The image management server 26 is a computer that stores and manages various data including the image captured using the modality 28 and comprises a high-capacity external storage device and a database management program. The image management server 26 communicates with other apparatuses through the local area network 29 and transmits and receives various data including image data. The image management server 26 receives the image data generated by the modality 28 and other various data via the local area network 29 and manages the data by storing the data in a storage medium such as the high-capacity external storage device.

The image processing distributor 24 included in the medical information system 20 of each medical institution is communicably connected to the central processing server 30 through a wide area network 120 such as the Internet. The wide area network 120 is an example of a "network outside a medical institution" and of a "second network" according to the embodiment of the present disclosure.

Configuration Example of Image Processing Distributor 24

The image processing distributor 24 can be implemented by a computer system configured using one or a plurality of computers. The function of the image processing distributor 24 is implemented by installing a program on the computer.

Figure 6:
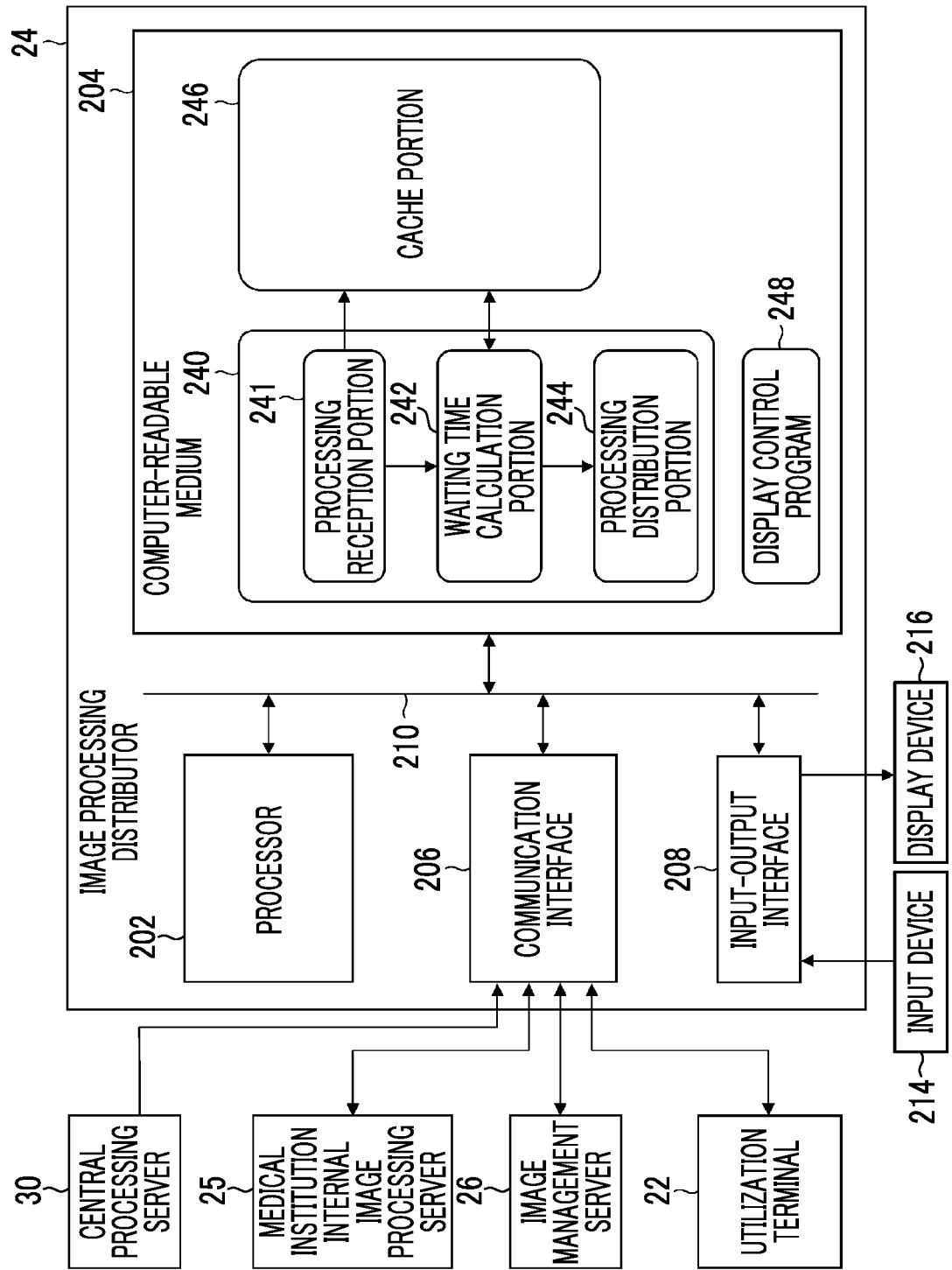
FIG. 6 is a block diagram illustrating a configuration example of the image processing distributor.

FIG. 6 is a block diagram illustrating a configuration example of the image processing distributor 24. The image processing distributor 24 includes a processor 202, a computer-readable medium 204 that is a non-transitory tangible object, a communication interface 206, an input-output interface 208, and a bus 210. The image processing distributor 24 may comprise an input device 214 and a display device 216. The input device 214 and the display device 216 are connected to the bus 210 through the input-output interface 208.

The image processing distributor 24 is communicably connected to the utilization terminal 22, the image management server 26, the medical institution internal image processing server 25, and the central processing server 30 through the communication interface 206.

The processor 202 includes a central processing unit (CPU). The processor 202 may include a graphics processing unit (GPU). The processor 202 is connected to the computer-readable medium 204, the communication interface 206, and the input-output interface 208 through the bus 210.

The computer-readable medium 204 includes a memory that is a main memory, and a storage that is an auxiliary storage device. For example, the computer-readable medium 204 may be a semiconductor memory, a hard disk drive (HDD) device, a solid state drive (SSD) device, or a combination of a plurality thereof. The computer-readable medium 204 is an example of a "storage device" according to the embodiment of the present disclosure.

The computer-readable medium 204 stores a plurality of programs including an image processing distribution program 240 and a display control program 248, data, and the like. The processor 202 functions as the processing reception portion 241, the waiting time calculation portion 242, and the processing distribution portion 244 by executing an instruction of the image processing distribution program 240. That is, the processor 202 executes the steps of the flowcharts described using FIG. 2 to FIG. 4.

The computer-readable medium 204 includes a cache portion 246. The cache portion 246 stores a cache file of data such as the image acquired by the image processing distributor 24. The cache portion 246 may store cache files of a plurality of medical images received by the image processing distributor 24 in the past. The cache files may be automatically deleted sequentially from the oldest cache file. In calculating the processing waiting time, the waiting time calculation portion 242 determines whether or not the processing target image is held in the cache portion 246.

The display control program 248 generates a display signal necessary for a display output for displaying the calculation results and the like of the waiting time calculation portion 242 on the display device 216 and/or on the utilization terminal 22 or the like, and performs a display control of the display device 216 or the like.

For example, the display device 216 is composed of a liquid crystal display, an organic electro-luminescence (OEL) display, a projector, or an appropriate combination thereof. For example, the input device 214 is composed of a keyboard, a mouse, a touch panel, other pointing devices, a voice input device, or an appropriate combination thereof. The input device 214 receives various inputs from an operator. The display device 216 and the input device 214 may be configured to be integrated using a touch panel.

Configuration Example of Medical Institution Internal Image Processing Server 25

The medical institution internal image processing server 25 can be implemented by a computer system configured using one or a plurality of computers. A processing function of the medical institution internal image processing server 25 is implemented by installing a program on the computer.

Figure 7:
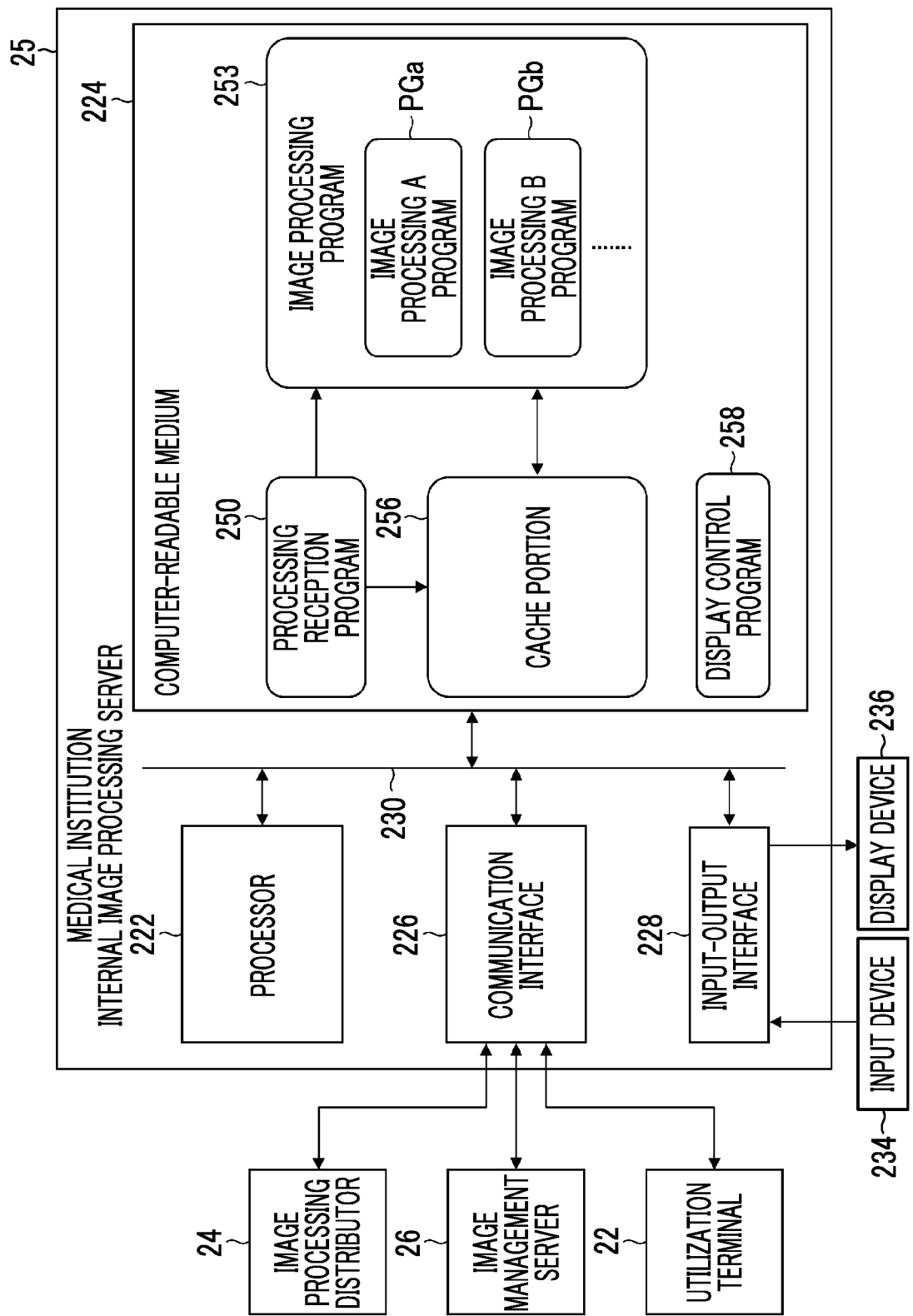
FIG. 7 is a block diagram illustrating a configuration example of the medical institution internal image processing server.

FIG. 7 is a block diagram illustrating a configuration example of the medical institution internal image processing server 25. The medical institution internal image processing server 25 includes a processor 222, a computer-readable medium 224 that is a non-transitory tangible object, a communication interface 226, an input-output interface 228, and a bus 230. The medical institution internal image processing server 25 may comprise an input device 234 and a display device 236. The input device 234 and the display device 236 are connected to the bus 230 through the input-output interface 228.

A hardware configuration of the medical institution internal image processing server 25 may be the same as a hardware configuration of the image processing distributor 24 described using FIG. 6. That is, a hardware configuration of each of the processor 222, the computer-readable medium 224, the communication interface 226, the input-output interface 228, the bus 230, the input device 234, and the display device 236 illustrated in FIG. 7 may be the same as a corresponding element thereof illustrated in FIG. 6.

The computer-readable medium 224 stores a plurality of programs including a processing reception program 250, an image processing program 253, and a display control program 258, data, and the like. The processor 222 functions as the processing reception portion 251 and as the image processing portion 252 by executing instructions of the processing reception program 250 and of the image processing program 253. The image processing program 253 may be configured to include a plurality of types of programs for performing a plurality of types of image processing. For example, the image processing program 253 includes a plurality of types of programs for image processing including an image processing A program PGa for performing the image processing A and an image processing B program PGb for performing the image processing B.

Specifically, for example, one or more programs including an organ segmentation program, a vascular region extraction program, a fracture CAD program, a bone labeling program, a lung nodule detection program, a lung nodule characteristics analysis program, a pneumonia CAD program, a lung segment labeling program, a mammary gland CAD program, a liver CAD program, a brain CAD program, a colon CAD program, and a report creation support program may be included as the program for image processing. These various programs may be AI processing modules including a trained model that is trained to obtain an output of a target task by applying machine learning such as deep learning.

For example, an AI model for CAD can be configured using various convolutional neural networks (CNNs) having a convolutional layer. For example, input data for the AI model may include the medical image such as a two-dimensional image, a three-dimensional image, or a motion picture image, and an output from the AI model may be information indicating a position of a disease region (lesion part) in the image, information indicating a classification such as a disease name, or a combination thereof.

A combination of the processing reception program 250 and the image processing program 253 is an example of a "server program" according to the embodiment of the present disclosure.

The computer-readable medium 224 includes the cache portion 246. The cache portion 246 stores a cache file of data such as the image acquired by the medical institution internal image processing server 25. A cache function using the cache portion 246 is the same as the cache function described using FIG. 6. In calculating the processing waiting time, the image processing distributor 24 determines whether or not the processing target image is stored in the cache portion 246.

The display control program 258 generates a display signal necessary for a display output for displaying a processing result and the like of the image processing program 253 on the display device 236 and/or on the utilization terminal 22 or the like, and performs a display control of the display device 236 or the like.

Configuration Example of Central Processing Server 30

The central processing server 30 can be implemented by a computer system configured using one or a plurality of computers. A processing function of the central processing server 30 is implemented by installing a program on the computer.

Figure 8:
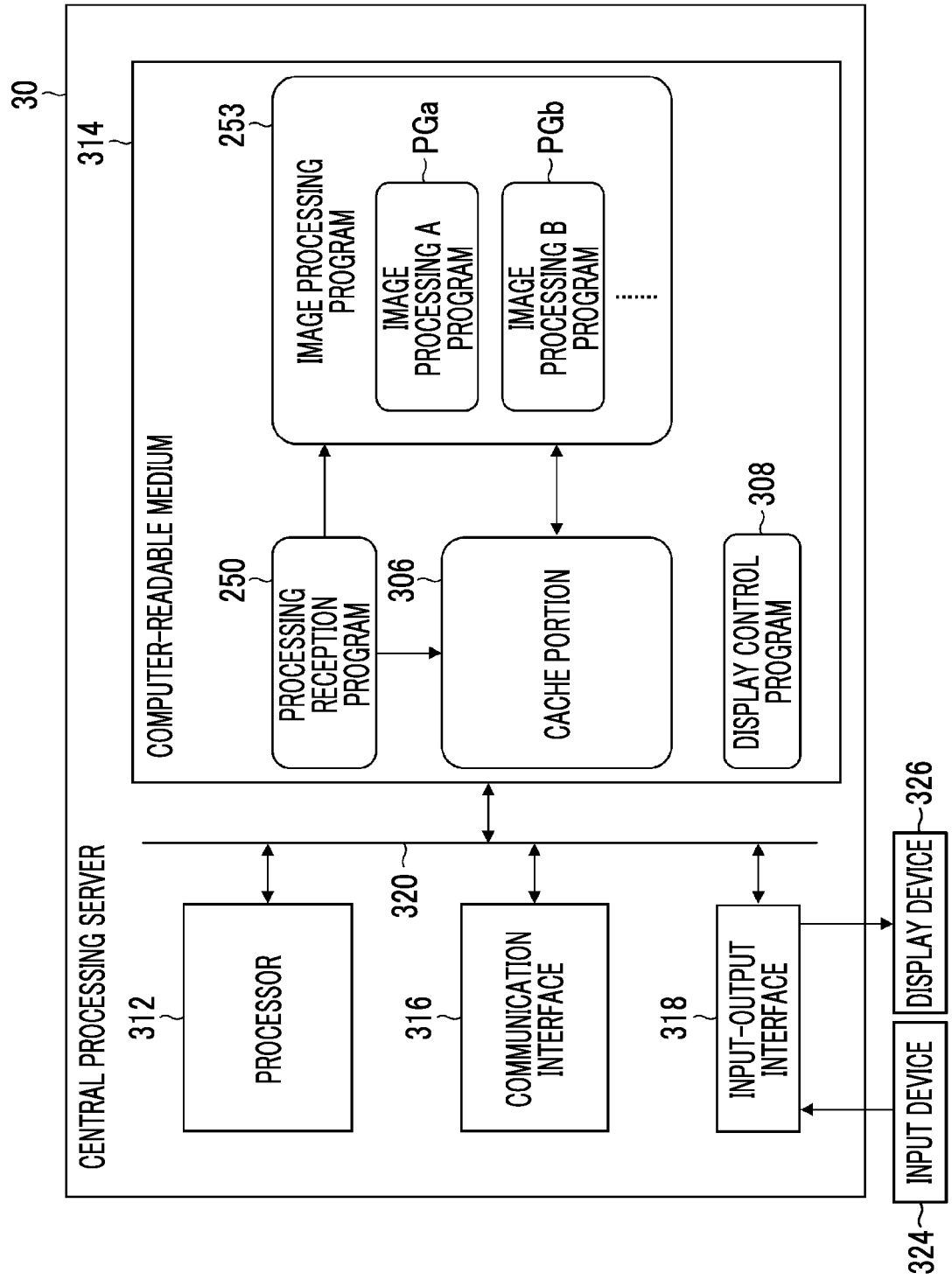
FIG. 8 is a block diagram illustrating a configuration example of the central processing server.

FIG. 8 is a block diagram illustrating a configuration example of the central processing server 30. The central processing server 30 includes a processor 312, a computer-readable medium 314 that is a non-transitory tangible object, a communication interface 316, an input-output interface 318, and a bus 320. The central processing server 30 may comprise an input device 324 and a display device 326. The input device 324 and the display device 326 are connected to the bus 320 through the input-output interface 318. A hardware configuration of the central processing server 30 may be the same as the hardware configuration of the medical institution internal image processing server 25 described using FIG. 7. That is, a hardware configuration of each of the processor 312, the computer-readable medium 314, the communication interface 316, the input-output interface 318, the bus 320, the input device 324, and the display device 326 illustrated in FIG. 8 may be the same as a corresponding element thereof illustrated in FIG. 7.

In addition, as in FIG. 7, the computer-readable medium 314 stores a plurality of programs including the processing reception program 250, the image processing program 253, and a display control program 308, data, and the like. The processor 312 functions as the processing reception portion 301 and as the image processing portion 302 by executing the instructions of the processing reception program 250 and of the image processing program 253.

The computer-readable medium 314 includes a cache portion 306. The cache portion 306 stores a cache file of data such as the image acquired by the central processing server 30. A cache function using the cache portion 306 is the same as the cache function described using FIG. 6. In calculating the processing waiting time, the image processing distributor 24 (refer to FIG. 1) of each medical institution determines whether or not the processing target image is stored in the cache portion 306.

The display control program 308 generates a display signal necessary for a display output for displaying the processing result and the like of the image processing program 253 on the display device 326 and/or on the utilization terminal 22 or the like, and performs a display control of the display device 326 or the like.

Modification Example 1

In the embodiment, while an example in which each of the image processing distributor 24, the medical institution internal image processing server 25, and the central processing server 30 has the cache function is described, a configuration in which some or all of the image processing distributor 24, the medical institution internal image processing server 25, and the central processing server 30 do not have the cache function is also possible.

In a case where the image processing distributor 24 does not have the cache function, a configuration not including the cache portion 246 illustrated in FIG. 6 is provided. Similarly, in a case where the medical institution internal image processing server 25 does not have the cache function, a configuration not including a cache portion 256 illustrated in FIG. 7 is provided. In a case where the central processing server 30 does not have the cache function, a configuration not including a cache portion 306 illustrated in FIG. 8 is provided.

Figure 9:
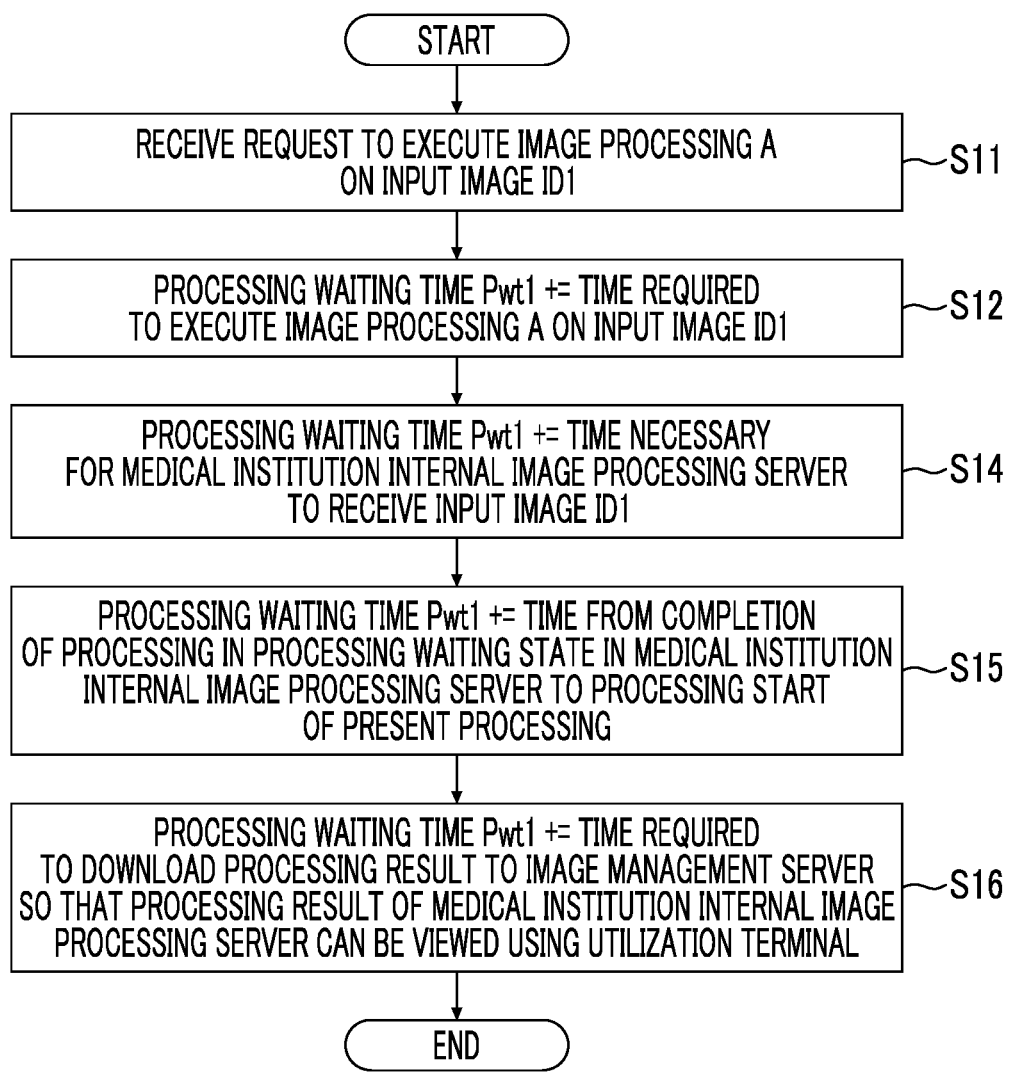
FIG. 9 is a flowchart illustrating a calculation example of the waiting time executed in a waiting time calculation portion in a case where the medical institution internal image processing server does not have a cache function.

In a case where the medical institution internal image processing server 25 does not have the cache function, the waiting time calculation portion 242 executes the flowchart in FIG. 9 instead of the flowchart in FIG. 2. In FIG. 9, steps identical to FIG. 2 are designated by the identical step numbers, and duplicate description will be omitted. In the flowchart in FIG. 9, step S13 in FIG. 2 is deleted, and the processing path transitions to step S14 after step S12. Other steps are the same as in FIG. 2.

Figure 10:
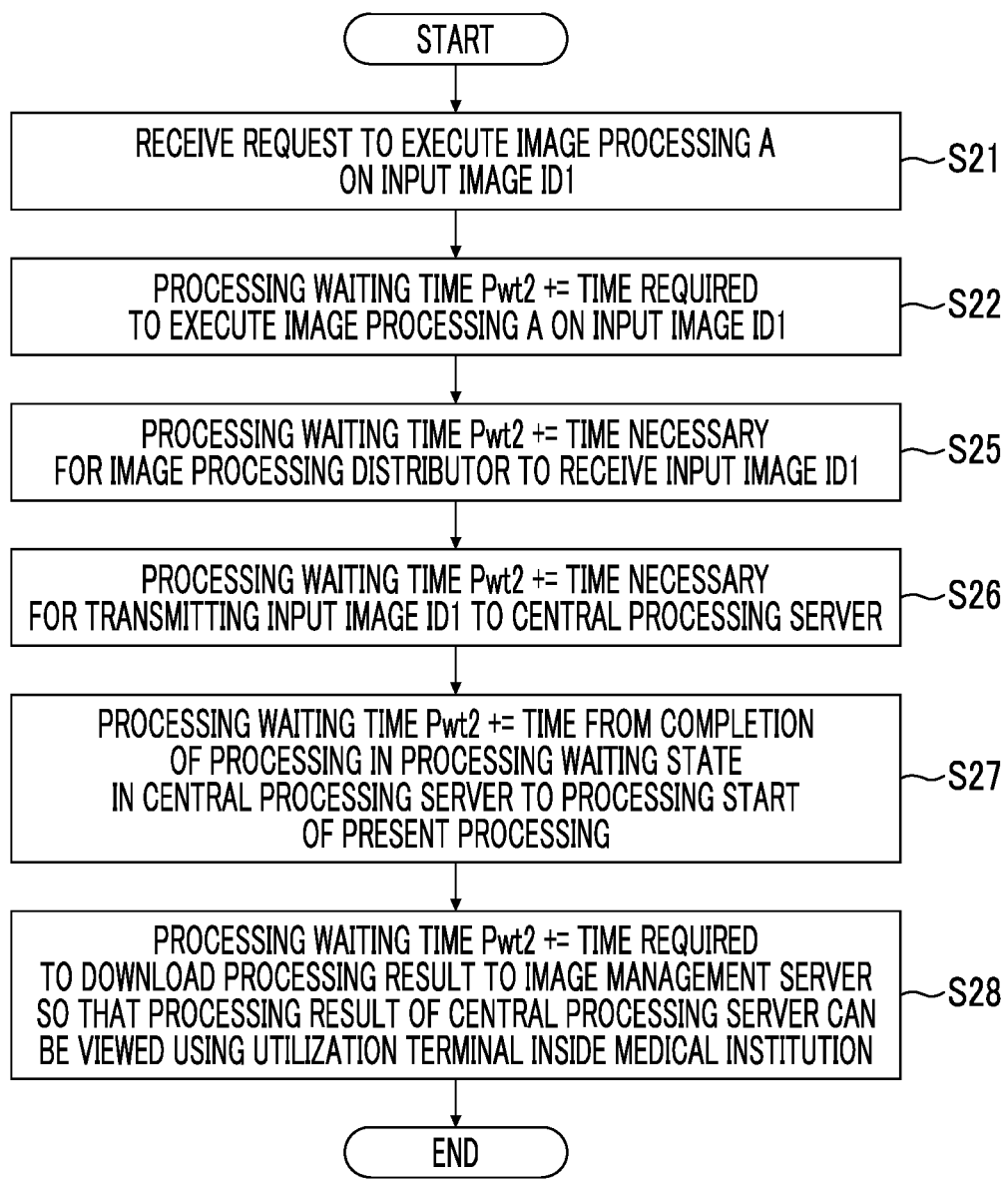
FIG. 10 is a flowchart illustrating a calculation example of the waiting time executed in the waiting time calculation portion in a case where the image processing distributor and the central processing server do not have the cache function.

FIG. 10 is a flowchart illustrating a calculation example of the waiting time executed in the waiting time calculation portion 242 in a case where any of the image processing distributor 24 and the central processing server 30 does not have the cache function.

In FIG. 10, in a case where any of the image processing distributor 24 and the central processing server 30 does not have the cache function, the waiting time calculation portion 242 executes the flowchart in FIG. 10 instead of the flowchart in FIG. 3. In FIG. 10, steps identical to FIG. 3 are designated by the identical step numbers, and duplicate description will be omitted. In the flowchart in FIG. 10, step S23 and step S24 in FIG. 3 are deleted, and the processing path transitions to step S25 after step S22. Other steps are the same as in FIG. 3.

Modification Example 2

In the embodiment, while an example in which the image processing distributor 24 is constructed as a server separated from the medical institution internal image processing server 25 is described, the image processing distributor 24 may be constructed on the same server as the medical institution internal image processing server 25.

Program Operating Computer

A program causing a computer to implement a part or all of at least one processing function of various processing functions in the medical image processing system 10 described in the embodiment and the modification examples can be recorded on a computer-readable medium that is an optical disc, a magnetic disk, a semiconductor memory, or another tangible non-transitory information storage medium, and the program can be provided through the information storage medium.

In addition, instead of an aspect of providing the program by storing the program in the tangible non-transitory computer-readable medium, a program signal can be provided as a download service by utilizing an electric communication line such as the Internet.

Hardware Configuration of Each Processing Unit

For example, a hardware structure of a processing unit executing various processing of the processing reception portion 241, the waiting time calculation portion 242, the processing distribution portion 244, the processing reception portion 251, the image processing portion 252, the processing reception portion 301, the image processing portion 302, and the like in the medical image processing system 10 include the following various processors.

The various processors include a CPU that is a general-purpose processor functioning as various processing units by executing a program, a GPU that is a processor specialized in image processing, a programmable logic device (PLD) such as a field programmable gate array (FPGA) that is a processor of which a circuit configuration can be changed after manufacturing, a dedicated electric circuit such as an application specific integrated circuit (ASIC) that is a processor having a circuit configuration dedicatedly designed to execute specific processing, and the like.

One processing unit may be composed of one of the various processors or may be composed of two or more processors of the same type or different types. For example, one processing unit may be composed of a plurality of FPGAs, a combination of a CPU and an FPGA, or a combination of a CPU and a GPU. In addition, a plurality of processing units may be composed of one processor. Examples of the plurality of processing units composed of one processor include, first, as represented by a computer such as a client or a server, a form in which one processor is composed of a combination of one or more CPUs and software, and this processor functions as the plurality of processing units. Second, as represented by a system on chip (SoC) or the like, a form of using a processor that implements functions of the whole system including the plurality of processing units via one integrated circuit (IC) chip is included. Accordingly, various processing units are configured using one or more of the various processors as a hardware structure.

Furthermore, the hardware structure of the various processors is more specifically an electric circuit (circuitry) in which circuit elements such as semiconductor elements are combined.

Advantages of Medical Image Processing System 10 According to Embodiment

According to the medical image processing system 10, the following advantages are achieved.

[1] The processing waiting time of the image processing by each server of the medical institution internal image processing server 25 and of the central processing server 30 is calculated in accordance with a situation of the medical institution internal image processing server 25 for each medical institution, a network connecting situation inside and outside the medical institution, and a situation of the central processing server 30. Accordingly, the processing waiting time can be appropriately predicted in accordance with a dynamically changing situation.

[2] In addition, the processing waiting time until the processing result is output with respect to the received processing request can be suppressed by distributing the processing request such that a server having a shorter calculated processing waiting time executes the image processing.

[3] According to the medical image processing system 10, the processing request can be distributed to the medical institution internal image processing server 25 or to the central processing server 30 to minimize the waiting time in accordance with a situation.

Other

The present disclosure is not limited to the contents of the embodiment and of the modification examples, and various modifications can be made without departing from the gist of the technical idea of the present disclosure.

EXPLANATION OF REFERENCES

10: medical image processing system
20: medical information system
22: utilization terminal
24: image processing distributor
25: medical institution internal image processing server
26: image management server
27: electronic medical record system
28: modality
29: local area network
30: central processing server
120: wide area network
202: processor
204: computer-readable medium
206: communication interface
208: input-output interface
210: bus
214: input device
216: display device
222: processor
224: computer-readable medium
226: communication interface
228: input-output interface
230: bus
234: input device
236: display device
240: image processing distribution program
241: processing reception portion
242: waiting time calculation portion
244: processing distribution portion
246: cache portion
248: display control program
250: processing reception program
251: processing reception portion
252: image processing portion
253: image processing program
256: cache portion
258: display control program
301: processing reception portion
302: image processing portion
306: cache portion
308: display control program
312: processor
314: computer-readable medium
316: communication interface
318: input-output interface
320: bus
324: input device
326: display device
PGa: image processing A program
PGb: image processing B program
Pwt1: time
Pwt2: time
S11 to S15: step of processing waiting time calculation flow in case of performing image processing in medical institution internal image processing server
S21 to S28: step of processing waiting time calculation flow in case of performing image processing in central processing server
S31 to S34: step of processing executed by processing distribution portion

What is claimed is:

1. A medical image processing system comprising:
a first server installed inside a medical institution;
a second server installed on a network outside the medical institution; and
an image processing distributor that distributes a processing request for a medical image to the first server or to the second server,
wherein each of the first server and the second server includes a server program that receives the processing request for the medical image and that outputs a processing result by executing image processing corresponding to the processing request,
the image processing distributor includes one or more processors and one or more storage devices in which a program executed by the one or more processors is stored, and
the one or more processors are configured to, by executing an instruction of the program,
receive the processing request for the medical image,
calculate a processing waiting time required until the processing result is obtained in a case where each server of the first server and the second server executes the image processing on the medical image, based on a required time required for executing the image processing on the medical image, a network connecting situation, and a number of processing requests in a processing waiting state inside each server, and
transmit the processing request for the medical image to a server having a shorter processing waiting time out of the first server and the second server based on the calculated processing waiting time for each server,
wherein the one or more processors are configured to calculate
a first processing waiting time required until the processing result is obtained in a case of executing the image processing via the first server, and
a second processing waiting time required until the processing result is obtained in a case of executing the image processing via the second server, and
decide a transmission destination of the processing request based on a comparison between the calculated first processing waiting time and the calculated second processing waiting time.

2. The medical image processing system according to claim 1,
wherein the second server is shared and used by a plurality of the medical institutions.

3. The medical image processing system according to claim 1, wherein the image processing distributor receives the processing request for the medical image from a terminal connected to a first network inside the medical institution.

4. The medical image processing system according to claim 2,
wherein the image processing distributor receives the processing request for the medical image from a terminal connected to a first network inside the medical institution.

5. The medical image processing system according to claim 1,
wherein an image management server that stores the medical image is installed inside the medical institution.

6. The medical image processing system according to claim 2,
wherein an image management server that stores the medical image is installed inside the medical institution.

7. The medical image processing system according to claim 3,
wherein an image management server that stores the medical image is installed inside the medical institution.

8. The medical image processing system according to claim 4,
wherein an image management server that stores the medical image is installed inside the medical institution.

9. The medical image processing system according to claim 5,
wherein the processing result of the image processing executed by the first server or by the second server is stored in the image management server.

10. The medical image processing system according to claim 6,
wherein the processing result of the image processing executed by the first server or by the second server is stored in the image management server.

11. The medical image processing system according to claim 7,
wherein the processing result of the image processing executed by the first server or by the second server is stored in the image management server.

12. The medical image processing system according to claim 8,
wherein the processing result of the image processing executed by the first server or by the second server is stored in the image management server.

13. The medical image processing system according to claim 1,
wherein the second server acquires the medical image from the image processing distributor through a second network as the network outside the medical institution.

14. The medical image processing system according to claim 2,
wherein the second server acquires the medical image from the image processing distributor through a second network as the network outside the medical institution.

15. The medical image processing system according to claim 1,
wherein at least one of the first server, the second server, or the image processing distributor holds a cache file of the medical image received in the past.

16. The medical image processing system according to claim 1,
wherein the one or more processors are configured to calculate the processing waiting time based on whether or not transmission and reception of the medical image that is a processing target are necessary.

17. A medical image processing method executed by a computer system including a first server installed inside a medical institution, and a second server installed on a network outside the medical institution, each of the first server and the second server including a server program that receives a processing request for a medical image and that outputs a processing result by executing image processing corresponding to the processing request, the medical image processing method comprising:
via one or more processors included in the computer system,
receiving the processing request for the medical image;
calculating a processing waiting time required until the processing result is obtained in a case where each server of the first server and the second server executes the image processing on the medical image, based on a required time required for executing the image processing on the medical image, a network connecting situation, and a number of processing requests in a processing waiting state inside each server; and
transmitting the processing request for the medical image to a server having a shorter processing waiting time out of the first server and the second server based on the calculated processing waiting time for each server,
wherein the one or more processors are configured to calculate
a first processing waiting time required until the processing result is obtained in a case of executing the image processing via the first server, and
a second processing waiting time required until the processing result is obtained in a case of executing the image processing via the second server, and
decide a transmission destination of the processing request based on a comparison between the calculated first processing waiting time and the calculated second processing waiting time.

18. An image processing distributor that distributes a processing request for a medical image to a first server installed inside a medical institution or to a second server installed on a network outside the medical institution, each of the first server and the second server including a server program that receives the processing request for the medical image and that outputs a processing result by executing image processing corresponding to the processing request, the image processing distributor comprising:
one or more processors and one or more storage devices in which a program executed by the one or more processors is stored,
wherein the one or more processors are configured to, by executing an instruction of the program,
receive the processing request for the medical image,
calculate a processing waiting time required until the processing result is obtained in a case where each server of the first server and the second server executes the image processing on the medical image, based on a required time required for executing the image processing on the medical image, a network connecting situation, and a number of processing requests in a processing waiting state inside each server, and
transmit the processing request for the medical image to a server having a shorter processing waiting time out of the first server and the second server based on the calculated processing waiting time for each server, wherein the one or more processors are configured to calculate
- a first processing waiting time required until the processing result is obtained in a case of executing the image processing via the first server, and
- a second processing waiting time required until the processing result is obtained in a case of executing the image processing via the second server, and
- decide a transmission destination of the processing request based on a comparison between the calculated first processing waiting time and the calculated second processing waiting time.

19. A non-transitory computer readable recording medium storing a program that causes a computer to implement a function of receiving a processing request for a medical image, and a function of distributing the received processing request to a first server installed inside a medical institution or to a second server installed on a network outside the medical institution, each of the first server and the second server including a server program that outputs a processing result by executing image processing corresponding to the processing request, the program causing the computer via one or more processors to implement:

- a function of calculating a processing waiting time required until the processing result is obtained in a case where each server of the first server and the second server executes the image processing on the medical image, based on a required time required for executing the image processing on the medical image, a network connecting situation, and a number of processing requests in a processing waiting state inside each server; and
- a function of transmitting the processing request for the medical image to a server having a shorter processing waiting time out of the first server and the second server based on the calculated processing waiting time for each server, wherein the one or more processors are configured to calculate
- a first processing waiting time required until the processing result is obtained in a case of executing the image processing via the first server, and
- a second processing waiting time required until the processing result is obtained in a case of executing the image processing via the second server, and
- decide a transmission destination of the processing request based on a comparison between the calculated first processing waiting time and the calculated second processing waiting time.

* * * * *